United States Patent [19]

Isaacson et al.

[11] Patent Number: 5,112,200
[45] Date of Patent: May 12, 1992

[54] HYDRODYNAMICALLY SUSPENDED ROTOR AXIAL FLOW BLOOD PUMP

[75] Inventors: Milton S. Isaacson; Anthony P. Lioi, both of Dayton, Ohio

[73] Assignee: Nu-Tech Industries, Inc., Dayton, Ohio

[21] Appl. No.: 529,598

[22] Filed: May 29, 1990

[51] Int. Cl.5 .............................................. F04B 17/00
[52] U.S. Cl. .................................... 417/356; 415/900; 604/151
[58] Field of Search ................ 417/354, 356; 415/900; 604/151; 600/16

[56] References Cited

U.S. PATENT DOCUMENTS

| 3,608,088 | 9/1971 | Dorman et al. | |
| 4,135,253 | 1/1979 | Reich et al. | 415/900 X |
| 4,332,199 | 5/1983 | Isaacson | 623/3 |
| 4,625,712 | 12/1986 | Wampler | 604/151 |
| 4,688,998 | 8/1987 | Olsen et al. | 417/356 |
| 4,704,121 | 11/1987 | Moise | 623/3 |
| 4,779,614 | 10/1988 | Moise | 600/16 |
| 4,817,586 | 4/1989 | Wampler | |
| 4,846,152 | 7/1989 | Wampler et al. | 600/16 |
| 4,895,557 | 1/1990 | Mosie et al. | 600/16 |
| 4,906,229 | 3/1990 | Wampler | 600/16 |
| 4,908,012 | 3/1990 | Moise et al. | 600/16 |
| 4,944,722 | 7/1990 | Carriker et al. | 600/16 |
| 4,957,504 | 9/1990 | Chardack | 623/3 |

Primary Examiner—Leonard E. Smith
Attorney, Agent, or Firm—Wood, Herron & Evans

[57] ABSTRACT

A brushless DC motor has a rotor with impeller blades mounted thereon to pump blood through the central portion of the motor. Over a portion of its length, the rotor has a cylindrical surface that is spaced from a cooperating cylindrical surface on the motor stator. There is a gap between these cylindrical surfaces through which there is a leakage flow of blood. The relative motion between the cylindrical surfaces provides a hydrodynamic bearing that suspends the rotor in the stator.

12 Claims, 2 Drawing Sheets

//5,112,200//

HYDRODYNAMICALLY SUSPENDED ROTOR AXIAL FLOW BLOOD PUMP

BACKGROUND OF THE INVENTION

This invention relates to a blood pump, and more particularly, to a combined pump and motor that is to be disposed in the bloodstream of a patient to pump or assist in the pumping of blood throughout the patient,s circulatory system.

It is desired that a motor/pump of this type have as small a size as possible consistent with the pumping requirements of the device. The suspension of the rotor with respect to the stator is a key to the miniaturization of the system. Where it is possible to minimize the structure by which the rotor is suspended with respect to the stator, it becomes possible to minimize the overall diameter of the motor and pump combination. It is also desired that a motor/pump of this type be constructed without radial seals that can break down and leak. Where it is possible to use a method of suspension of the rotor that operates in blood, the rotary seal can be avoided.

It has been an objective of the present invention to provide an improved rotor suspension system to minimize the size of the motor and pump combination, and to provide suspension without radial seals.

In accordance with the present invention, the stator has a cylindrical internal surface. The rotor has a cylindrical external surface that is substantially coextensive with the stator cylindrical surface. The rotor carries impeller blades to drive blood internally through the motor. There is a gap between the rotor and stator cylindrical surfaces.

During operation, the surfaces of the rotor and stator are so oriented that their relative motion produces a pressure distribution on the rotor that supports the rotor radially. The pressure distribution also creates a pumping action causing blood to flow through the gap between rotor and stator. Blood flow through this gap is further enhanced by the pressure generated axially across the rotor through the action of the impellers. The blood flowing axially through the rotor by the combined pumping action of the hydrodynamic bearing and the pressure generated by the impellers is hereinafter referred to as leakage flow. Since the gap between the rotor and stator is of the order of 0.008" in the radial direction, and since it is this gap with the blood flowing through that provides the suspension for the rotor, it can be seen that the rotor suspension is extremely small in the radial direction. Furthermore, because blood flows directly through the bearing, radial seals do not need to be included.

In the preferred form of the invention, the stator has axially-extending vanes at its inlet and outlet. These vanes have their radial inner edges pressed into the external surface of an elongated hub passing through the center of the rotor. Intermediate stator vanes, axially spaced from the inlet and outlet stator vanes, project radially outwardly from the hub. The rotor has an outside cylindrical surface that cooperates with a motor stator inside cylindrical surface, these surfaces being located between the inlet and outlet vanes. These surfaces create one location wherein the relative motion of mating surfaces provides a hydrodynamic bearing.

The hub has two axially spaced cylindrical surfaces. The rotor has two axially spaced sets of impeller blades that are mounted on the rotor and are terminated internally in a hub support cylinder. The support cylinder of each set of impeller blades cooperates with the hub cylinder to create radially inner gaps with mating surfaces that provide two additional hydrodynamic bearings.

Each of the cylindrical surfaces on the hub are in the form of an annular groove that is a shallow U-shape in longitudinal section. Similarly, the cylindrical surface of the stator is in the form of a shallow U-shaped annular groove in longitudinal section. These shallow U-shaped grooves axially capture the rotor and maintain it centered within the stator. The force of the impeller tends to drive the rotor axially as it rotates in its blood pumping function. That axial force is frictionally resisted by the engagement of radial surfaces between the rotor and the shallow grooves on the stator and hub. Alternatively, thrust-resisting magnets may be mounted in the stator support ring to form a thrust-resisting system.

In a motor pump of this type wherein blood is employed as a hydrodynamic bearing, shear stress should be high enough to provide forces that can prohibit cells from aggregating and thereby leading to thrombus formation. However, it is critically important to assure that shear stress is not so high as to cause blood cell destruction. Furthermore, cell destruction is due not only to shear stress, but also to exposure time of the cells to shear stress; thus, it is important to provide leakage flow high enough to minimize residence time of the cells in the gap. A level of shear stress and exposure time at approximately the threshold level for cell destruction will satisfy both requirements of minimizing thrombus formation and minimizing cell destruction. The parameters that contribute to shear stress are the gap size and the velocity. Residence time in the gap is dependent upon leakage flow, which in turn is dependent upon gap size. The larger the gap size, the lower is the shear stress and the higher is the leakage flow. In order to minimize cell damage in the gap, shear stress should be maintained below 2500 dynes per square centimeter and residence time of cells in the gap should be below 0.1 second. However, the gap size must be kept low to minimize violent eccentric motion of the rotor with respect to the stator.

Blood cell destruction within the main flow path of the pump, through the impeller and stator vanes, is also dependent upon shear stress. However, since the shear stress in the main flow path is not readily known, and since the velocity of a cell with respect to the pump surfaces affects shear stress, it is sufficient for the main flow path to minimize velocity as a means of minimizing cell destruction. Velocity should be below 1000 centimeters per second and preferably below 500 centimeters per second.

BRIEF DESCRIPTION OF THE DRAWINGS

The several features and objectives of the invention will become more readily apparent from the following detailed description taken in conjunction with the accompanying drawings in which.

DETAILED DESCRIPTION OF THE INVENTION

Figure 1:
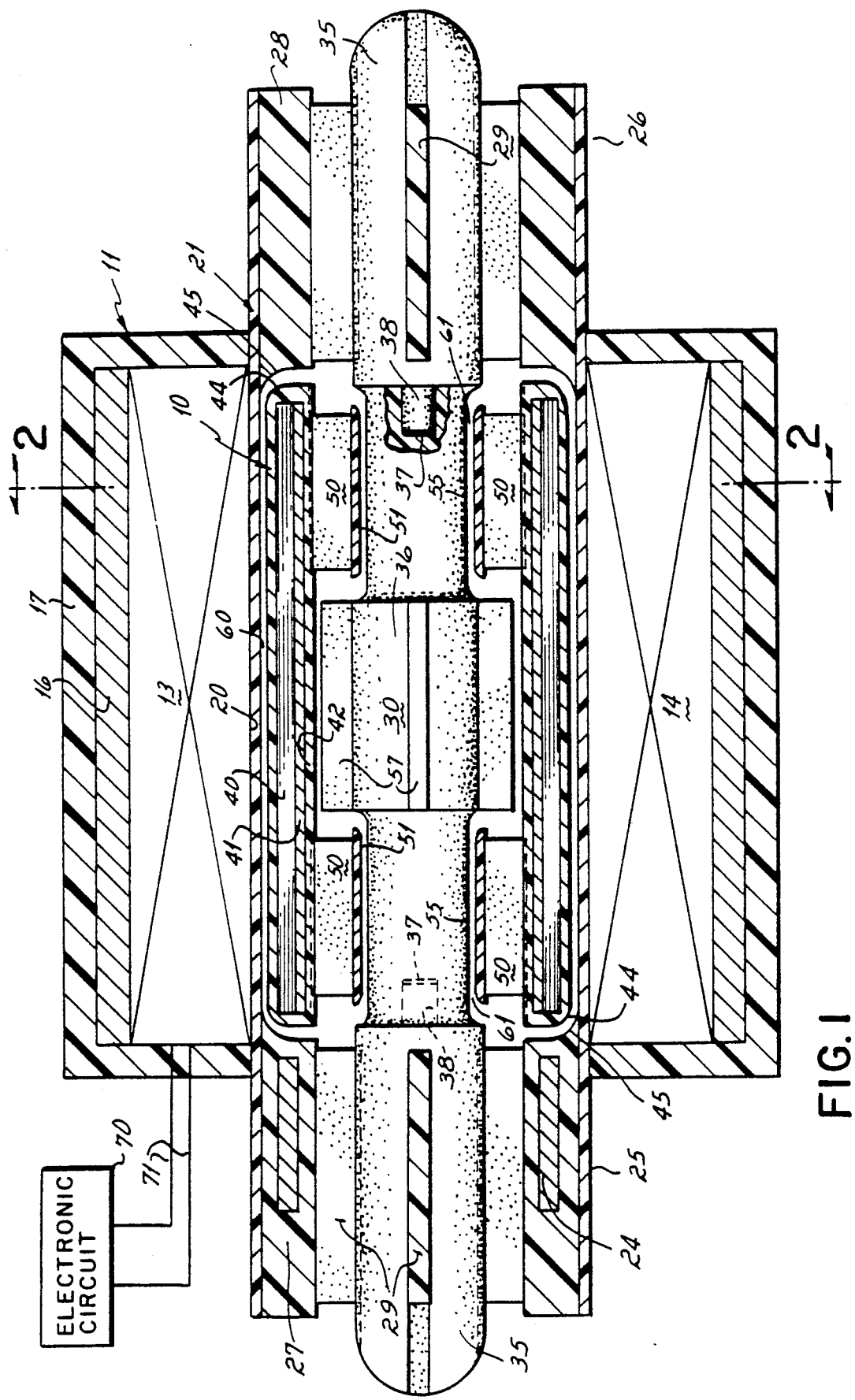
FIG. 1 is a diagrammatic longitudinal cross-sectional view through the center of the motor/pump combination.
Figure 2:
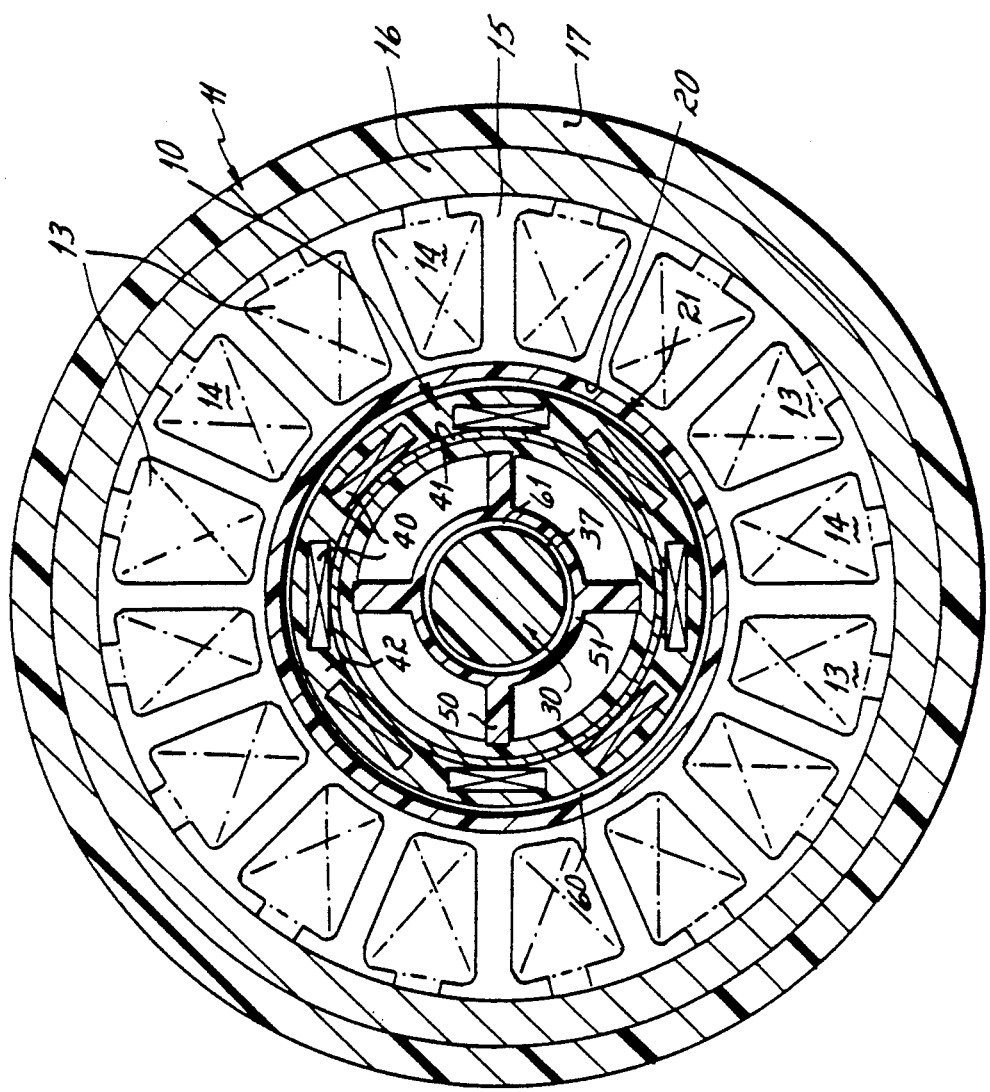
FIG. 2 is a cross-sectional view taken along lines 2—2 of FIG. 1.

Referring to the drawings, a rotor 10 is supported in a stator 11. In this embodiment, the stator has two phase windings 13 and 14 wound on a stator core 15. A metal yoke 16 surrounds the core and an epoxy capsulation 17 surrounds the metal yoke.

The stator has an internal cylindrical surface 20. A plastic housing 21 is press-fitted into the stator. Preferably, the plastic is a thermoplastic polyurethane (ISOPLAST 301 by Dow Chemical). The housing has an inlet 25 and an outlet 26. A stator support ring 27, having a thrust-resisting magnet 24, is fixed in the inlet and a stator support ring 28 is fixed in the outlet. Each stator support ring has six radial vanes 29. The inner ends of the stator vanes 29 are embedded in the surface of a plastic hub 30.

The plastic hub is actually in three sections. Identical inlet and outlet sections 35 are connected to a center section 36. The center section has recesses 37 at each end. The recesses receive studs 38 integral with the end sections 35.

The rotor 10 has eight axially-extending pole pieces 40 and a back iron ring 41 that are embedded in a cylinder of polyurethane plastic resin 42. The cylinder 42 is radiused at its ends as at 44. Similarly, the stator support rings 27 and 28 are radiused as at 45 to match the ends of the rotor plastic cylinder, thereby centering the rotor axially within the stator. The rotor has two sets of impeller blades 50 that are axially spaced from each other. The impeller blades have their inner ends mounted on a hub support cylinder 51. Their outer ends are embedded in the plastic cylinder 42. The hub 30 has a pair of annular grooves 55 into which the hub support cylinders 51 fit. Intermediate stator vanes 57 are mounted on the hub 30 and project into the space between the two sets of impeller blades. A cylindrical gap 60 is created between the cylindrical stator housing 21 and the plastic cylinder 42 of the rotor. That gap is preferably about 0.008" in radial dimension. An inner gap 61 is formed between each hub support cylinder 51 and annular groove 55. That gap is preferably about 0.004" in radial dimension. The motion of the rotor 10 within these gaps provides a pressure distribution on the rotor, thereby creating hydrodynamic bearings that maintain the rotor substantially centered radially in the stator. The length of each gap 60 is about 1". The length of the gap 61 is about 0.3". The inside diameter of the housing 21 is about 0.605". The diameter of the annular groove 55 is about 0.230".

To assemble the motor, the impeller blades 50 are pressed axially into the internal surface of the plastic cylinder 42 with the center hub section 36 carried between the impeller blades. The stator vanes 29 are axially-pressed into the hub sections 35. With the rotor centered in the housing 21, the assembly of stator support cylinders 27 and 28, vanes 29 and hub ends 35 are pressed into the housing until the studs 38 on the ends 35 seat in the recesses 37 of the hub center section 36.

In the illustrated embodiment, the intermediate stator vanes have free edges. It is contemplated that those stator vanes could be encased in a plastic ring, thus providing still another hydrodynamic bearing gap between the plastic ring on the stator and the plastic cylinder 42 on the rotor.

It should be understood that the impeller blades 50 are axially angulated so as to thrust fluid from the inlet end to the outlet end.

The stator is connected to an electronic circuit 70 by leads 71 and the brushless DC motor is operated generally in accordance with the principles of U.S. Pat. Nos. 4,027,215, 4,238,717 and U.S. Pat. No. 4,492,903 which are incorporated herein by reference.

In the operation of the invention, the motor is connected to the patient's circulatory system either externally or internally. A power supply and electronic circuit 70 connected to the motor drives the motor at a speed of about 16,500 rpm. The impeller blades on the rotor drive blood axially through the center of the motor, thereby substituting for or assisting the heart and maintaining the patient's needed circulation. The action of the impeller blades creates a high pressure at the outlet end of the rotor and a low pressure at the inlet end of the rotor. That high pressure causes leakage flow of blood through the gaps 60 and 61. It is calculated that the residence time of a cell in the gap 60 is about 0.034 seconds, and the residence time of a cell in each gap 61 is about 0.013 seconds. The shear stress in the gap 60 is about 1900 dynes per square centimeter, and the shear stress in the gap 61 is about 2200 dynes per square centimeter. The rotor surface forming the gaps 60 and 61 may have helical ribs to promote the flow of blood in an axial direction.

While the invention has been described in connection with the preferred embodiment which has a stator, a hollow rotor within the stator and a hub within the hollow rotor, it should be understood that the principles of the invention would be applicable to a motor/pump combination consisting of a stator, a hollow rotor and impeller blades within the hollow rotor, the stator having vanes at each end of the rotor. In this embodiment, there is only one gap to form the hydrodynamic bearings.

In still another embodiment of the invention, the stator windings are placed inside the hub 30. Permanent magnets are placed in the impeller hub 51 as closely adjacent to the hub 30 as possible to minimize the gap between the magnets and the windings of the stator.

Further, the invention has been described in connection with a two-stage pump, that is, a pump having two stages of impeller blades. To handle larger loads, the principles of the invention may be embodied in a three-stage pump wherein the rotor carries three stages of impeller blades. The preferred rotary speed for the two-stage motor/pump is about 16,500 rpm. The preferred speed for the three-stage motor/pump is about 12,700 rpm. The motor should pump about 6 liters per minute at 300 mmHg of pressure.

In one application of the invention, this will be a pump external to the body and it will be connected to the body just as the connections are made for heart-/lung bypass for a heart/lung machine. So this would be the heart of the heart/lung machine. It is also contemplated that the pump be inserted in a femoral artery and femoral vein in the leg. When it is implanted, the pump can be an implantable assist device or total artificial heart.

From the above disclosure of the general principles of the present invention and the preceding detailed description of a preferred embodiment, those skilled in the art will readily comprehend the various modifications to which the present invention is susceptible.

Therefore, we desire to be limited only by the scope of the following claims and equivalents thereof:

We claim:

1. A brushless DC motor and blood pump combination comprising:
   a sator having an axial cylindrical bore, said stator having windings and a control circuit to create flux in the said bore,
   a cylindrical rotor disposed in said bore and having permanent magnets spaced around its perimeter to interact with said flux to rotate said rotor,
   a gap of about 0.008 inch said rotor and said stator,
   said rotor having a central axial passageway for the passage of blood, impellers mounted on said rotor in said passageway to pump blood through said passageway as said rotor rotates,
   the relative motion between said rotor and said stator causing a pressure distribution in the blood within said gap that supports said rotor, thus forming a hydrodynamic bearing between said rotor and stator.

2. A motor as in claim 1 further comprising:
   magnets in said stator adjacent ne end of said rotor to repulse said rorot and form a thrust-resisting system.

3. A mtor as in claim 1 in which shear stress on blood cels within said gp is less than 2500 dynes/cm².

4. A motor as in claim 1 in which said rotot is rotated at a speed to maintain impeller tip speed below 1000 cm/sec., thereby avoiding significant blood cell destruction.

5. A motor/blood pump combination comprising:
   a stator having a bore,
   said stator including a central cylindrical hub within said bore,
   radial vanes fixedly connecting said hub to said stator at each end of said hub,
   a cylindrical rotor surrounding said hub and disposed within said bore,
   said rotor having permanent mgnets and said stator having windings and a circiut to create a brushless DC motor,
   impeller blades on said rotor to pump blood between said rotor and hub,
   and gaps between said hub and rotor and said rotor and stator through which said blood flows to provide hydro-dynamic bearings between said rotor and stator, and said rotor and hub,
   the pressure distribution in said gaps being generated by the relative motion between said rotor and said stator, and
   the pressure differential being generated axially across said rotor generted by the action of the impleelers,
   both pressure distribution and differential causing a leakage flow of blood through said gaps at a rate sufficient to prevent significant damage to blood cells from shear stress.

6. A motor as in claim 5 in which said rotor is rotated t about 16,500 rpm.

7. A motor as in claim 5 in which said gap size in the radial direction between rotor and stator is about 0.008 inch and in which gap size in the radial direction between rotor and hub is about 0.004 inch.

8. A motor as in claim 5 in which the average residence time of a cell in said gap between stator and rotor is about 0.034 seconds and in which the average residence time in said gap between said rotor and hub is about 0.013 seconds.

9. A motor as in claim 5 further comprising:
   a helical rib on at least one surface of said rotor to promote the axial movement of blood cells through said gap.

10. A motor as in claim 1 further comprising:
    axially-extending stator vanes at the inlet and outlet of said motor,
    intermediate stator vanes projecting radially from said hub and axially-sapced from said vanes at said inlet and outlet,
    two sets of rdially inwardly-directed impleeler blades on the internal surface of said rotor, one set of said impleller blades being located between said outlet vanes and said intermediate vanes, the other set being located between said inlet vanes and said intermediate vanes.

11. A motor as in claim 10 further comprising:
    an internal hub support cylinder on the radially inner ends of each set of said impeller blades,
    each said support cylinder creating with said hub one of said gaps through which blood flows.

12. A motor as in claim 6 wherein said hub has an annular groove that is a shallow U-shape in axial cross section to receive and center said rotor.

* * * * *

UNITED STATES PATENT AND TRADEMARK OFFICE
CERTIFICATE OF CORRECTION

Page 1 of 2

PATENT NO. : 5,112,200
DATED : 5-12-92
INVENTOR(S) : Milton S. Isaacson

It is certified that error appears in the above-identified patent and that said Letters Patent is hereby corrected as shown below:

Column 1, Line 9 should read "patient's" instead of "patient,s".

Column 5, Line 6 should read "stator having".

Column 5, Line 13 should read "inch between" instead of "inch said".

Column 6, Lines 7 and 8 should read "rotor generated . . . of the impellers . . .".

Column 6, Line 32-36 should read "axially spaced . . . radially . . . impeller blades . . . impeller blades . . .".

Claim 2, Column 5, Lines 24-25 should read "adjacent one end . . . said rotor" instead of "adjacent ne end . . said rorot. ".

Claim 3, Column 5, Line 27-28 should read "a motor . . . blood cells . . said gaps . . ". instead of "a mtor . . blood cels . . said gp . . ".

Claim 4, Column 5, Line 29 should read "rotor" instead of "rotot".

UNITED STATES PATENT AND TRADEMARK OFFICE
CERTIFICATE OF CORRECTION

PATENT NO. : 5,112,200
DATED : May 12, 1992
INVENTOR(S) : Milton S. Isaacson

It is certified that error appears in the above-indentified patent and that said Letters Patent is hereby corrected as shown below:

Claim 4, Column 6, Line 14 should read "rotated at about" instead of "rotated t about".

Signed and Sealed this

Seventeenth Day of August, 1993

Attest:

BRUCE LEHMAN

Attesting Officer

Commissioner of Patents and Trademarks